United States Patent [19]

Namekata et al.

[11] Patent Number: 5,416,256

[45] Date of Patent: May 16, 1995

[54] PROCESS FOR MANUFACTURING 5-HYDROXYISOPHTHALIC ACID

[75] Inventors: Takeshi Namekata; Ikuo Ito; Kazuhiko Maeda; Toshio Sato; Keiichi Yokota, all of Kashima, Japan

[73] Assignee: Sumikin Chemical Co., Ltd., Tokyo, Japan

[21] Appl. No.: 322,308

[22] Filed: Oct. 4, 1994

[30] Foreign Application Priority Data

Oct. 8, 1993 [JP] Japan ................... 5-277904

[51] Int. Cl.$^6$ ............................. C07C 51/16
[52] U.S. Cl. ................................... 562/416
[58] Field of Search ........................ 562/416

[56] References Cited

U.S. PATENT DOCUMENTS 4,263,452  4/1981  Komatsu ............... 562/482

FOREIGN PATENT DOCUMENTS 223522   6/1958  Australia .
2104909  9/1972  Germany .
9133347 12/1974  Japan .
2242644 10/1987  Japan .
807091   1/1959  United Kingdom .
837321   6/1960  United Kingdom .

Primary Examiner—Paul J. Killos
Attorney, Agent, or Firm—Wenderoth, Lind & Ponack

[57] ABSTRACT

An improved process for manufacturing 5-hydroxyisophthalic acid by means of oxidizing 5-acyloxy-m-xylene or its oxidation intermediate with molecular oxygen in a solvent consisting of lower aliphatic carboxylic acid and acetic anhydride in the presence of catalyst consisting of heavy metal comprising cobalt as the main component, and a bromine compound, and hydrolyzing the product thereby obtained. The improvement is characterized in that the oxidation is carried out under a pressure of 2-15/cm$^2$ gauge in the presence of an alkali metal compound corresponding to 0.1-1.1 gram atom in terms of alkali metal atom based upon 1 gram atom of the heavy metal used for the catalyst.

The present invention produces a high-quality 5-hydroxyisophthalic acid having excellent color from 5-acyloxy-m-xylene.

6 Claims, No Drawings

PROCESS FOR MANUFACTURING 5-HYDROXYISOPHTHALIC ACID

BACKGROUND OF THE INVENTION

1. Field of the Invention

The present invention relates to an improved process for manufacturing 5-hydroxyisophthalic acid (hereinafter referred to as "5-HIPA"), which is useful as a raw material for producing high-performance polymers, pharmaceuticals and agrochemicals.

2. Description of the Related Art

It is well known that 5-HIPA can be produced by alkali fusion of 5-sulfoisophthalic acid. Nevertheless, this method poses major technical problems, for example, large amounts of fuming sulfuric acid or alkaline material such as caustic soda have to be used, the sulfonation reaction affords only poor selectivity, large amounts of by-products are produced in the alkali fusion step, and the reaction is required to proceed at a high temperature as well as under high pressure, thus rendering it quite difficult to inexpensively produce high-purity 5-HIPA in a large quantity.

It is also public knowledge that 5-HIPA can be produced by oxidizing 5-acyloxy-m-xylene with molecular oxygen in the presence of lower aliphatic carboxylic acid and acetic anhydride, using a cobalt compound and a bromine compound, or a cobalt compound, a manganese compound and a bromine compound. (Japanese Patent Publication No. Sho-57 (1982)-15737.) Since the above-mentioned method is, however, an oxidation reaction carried out under an elevated pressure of 20–50 kg./$cm^2$ gauge, using either oxygen or air, the 5-acyloxy- isophthalic acid thus produced exhibits a poor color. That is to say, the product is discolored in that it is yellowish brown or gray, and the method by itself gives an insufficient yield. Even if such discolored 5-acyloxyisophthalic acid is hydrolyzed, there cannot be obtained 5-HIPA that can be utilized as the raw material for high performance polymers, pharmaceuticals or agrochemicals.

The present inventors have arrived at the present invention by discovering means by which to resolve the above-mentioned problems after intensive study.

In fact, the present inventors have discovered that the above-mentioned problems can be resolved by oxidizing with air 5-acyloxy-m-xylene at a pressure of 2–15 kg./$cm^2$ gauge which is lower than the conventionally adopted pressure level in the presence of lower aliphatic carboxylic acid and acetic anhydride, with a catalyst system consisting of a cobalt compound and a bromine compound, while letting a specific amount of alkali metal compound coexist with the reaction system.

Hence, the object of the present invention is to provide a method for producing at a high yield and more inexpensively, 5-HIPA that can be utilized as the raw material for high-performance polymers, pharmaceuticals or agrochemicals by means of air-oxidizing 5-acyloxy-m-xylene in the liquid phase.

SUMMARY OF THE INVENTION

The present invention relates to a process for manufacturing 5-hydroxyisophthalic acid which comprises oxidizing with molecular oxygen 5-acyloxy-m-xylene or its oxidation intermediates in a solvent consisting of lower aliphatic carboxylic acid and acetic anhydride in the presence of a catalyst consisting of heavy metal compounds, wherein cobalt being its main component, and a bromine compound, and hydrolyzing the product thereby obtained. The process is characterized in that the oxidation is carried out under a pressure of 2–15 kg/$cm^2$ gauge in the presence of an alkali metal compound corresponding to 0.1–1.1 gram atom in terms of alkali metal atom based upon 1 gram atom of the heavy metal in the catalyst.

DESCRIPTION OF THE PREFERRED EMBODIMENT 5-acyloxy-m-xylene which is utilized as the raw material for the oxidation step in the present invention, is obtained by esterifying 3,5-dimethyl phenol with carboxylic acid, carboxylic anhydride or acid chloride. Carboxylic anhydride in the liquid state is preferably used as the esterification agent, since in such a case the esterification reaction mixture can be used as it is as the raw material for the oxidation step.

For instance, although 5-acetoxy-m-xylene can be obtained by reacting 3,5-dimethylphenol with excess acetic anhydride and then distilling the reaction product upon completion of the reaction, it is also possible that such reaction product is used as the raw material for the oxidation step without the distillation step.

The carboxylic acid used for esterifying 3,5-dimethylphenol is aliphatic carboxylic acid such as acetic acid, propionic acid, and burytic acid. The carboxylic anhydride used for esterifying 3,5-dimethylphenol is anhydride such as acetic anhydride, propionate anhydride, and burytic anhydride. Furthermore, the acid chloride used for the esterification is chloride of aliphatic carboxylic acid such as acetyl chloride, propionyl chloride, and butanoyl chloride.

Oxidation intermediates of 5-acyloxy-m-xylene, such as 5-acyloxy-m-toluic acid can also be used as the raw material for the oxidation step.

The lower aliphatic carboxylic acids which can be used as the solvent in the present invention are acetic acid, propionic acid and butyric acid, among which acetic acid, propionic acid or a mixture thereof are preferably used.

While acetic anhydride is added to the above-mentioned lower aliphatic carboxylic acid as the solvent in the present invention, the preferable amount of acetic anhydride to be added is 2 mol or more per mol of 5-acyloxy-m-xylene, The amount of solvent thus prepared, consisting of lower aliphatic carboxylic acid and acetic anhydride, is preferably in terms of the 5-acyloxy-m-xylene concentration 0.2–2.0 mol of 5-acyloxy-m-xylene per kg. of solvent, more preferably 0.4–1.4 mol of 5-acyloxy-m-xylene per kg. of solvent. If the 5-acyloxy-m-xylene concentration exceeds 2.0 mol per kg. of solvent, the 5-acyloxyisophthalic acid yield decreases.

According to the present invention, a catalyst consisting of a heavy metal compound, of which cobalt is the principal component, and a bromine compound is used. The components of the catalyst are combined in the following manner.

The cobalt compound may be any such cobalt compound that is soluble in a solvent consisting of lower aliphatic carboxylic acid and acetic anhydride. There can be cited as examples of such compounds acetate, carbonate, hydroxide, and bromide. The amount of cobalt compound to be added is preferably 0.4–8% by weight as cobalt, and more preferably 0.6–5.4% by weight as cobalt as against 5-acyloxy-m-xylene. It is also possible to prepare such heavy metal catalyst by co-using a manganese compound and a cerium compound in addition to the cobalt compound.

For the bromine compound, potassium bromide, sodium bromide or ammonium bromide may be used. The amount of bromine compound to be added is preferably 0.5–15% by weight as against 5-acyloxy-m-xylene, but more preferably 0.9–12% by weight.

According to the present invention, 5-acyloxyisophthalic acid, which is the oxidation reaction product, can be produced having an improved color and an increased yield by means of causing an alkali metal compound to co-exist with the reaction system, in addition to the solvent consisting of lower aliphatic carboxylic acid and acetic anhydride and the catalyst comprising as its principal component a cobalt compound and a bromine compound. The alkali metal compounds suitably used for the above-mentioned purpose are bromide, acetate, carbonate and hydroxide. The amount of alkali metal compound to be added is 0.1–1.1 gram atom in terms of alkali metal atom based upon 1 gram atom of the heavy metal to be used for the catalyst, but more preferably 0.5–1.0 gram atom. If the content level is lower than 0.1 gram atom, high-quality 5-acyloxyisophthalic acid cannot be obtained, because the color-improving effect diminishes and the yield decreases. Any content level in excess of 1.1 gram atom is not desirable, since at such content level the catalyst activity declines and the yield of 5-acyloxyisophthalic acid decreases.

The reaction temperature is generally 60°–150° C., but preferably 95°–125° C. If the reaction temperature is higher than this level, the yield of 5-acyloxyisophthalic acid decreases.

According to the present invention, the resulting 5-acyloxyisophthalic acid has an improved color by means of having alkali metal compound co-exist with the reaction system and maintaining the reaction pressure within the range of 2–15 kg./cm$^2$ gauge, preferably 5–12 kg/cm$^2$ gauge.

Although it has been conventionally believed that a high reaction pressure is indispensable for achieving a high yield in this kind of oxidation reaction, the high reaction pressure conventionally adopted for the oxidation reaction involving 5-acyloxy-m-xylene, i.e. at 15 kg/cm$^2$ gauge or higher, is not desirable at all, since the yield of 5-acyloxyisophthalic acid decreases due to side reactions, such as cleavage and polymerization accompanying the cleavage or condensation of 5-acyloxyisophthalic acid and oxidation intermediates, which are carried out due to such high reaction pressure along with discoloration of the obtained 5-acyloxyisophthalic acid, in spite of an increased rate of oxidation reaction owing to the elevated oxygen partial pressure.

The present invention is based on the discovery that the intended product can be obtained at a better yield using a lower reaction pressure than that which is adopted conventionally by virtue of the presence of a specific amount of alkali metal compound. Side reactions are prevented and both yield and product quality are improved by means of lowering the reaction pressure.

Nevertheless, any reaction pressure lower than 2 kg/cm$^2$ gauge is not desirable from an industrial point of view, since the oxidation reaction rate decreases in such a case.

The 5-acyloxyisophthalic acid thus obtained can be converted into 5-HIPA by hydrolyzing it by the conventional method.

The present invention shall be explained in detail with the following examples:

EXAMPLE 1

A 0.5 liter titanium autoclave, provided with a reflux condenser, a gas feed tube, and an agitator was charged with 170 g. of acetic acid and 70 g. of acetic anhydride as solvent, 1.40 g. of cobalt acetate tetrahydrate and 0.67 g. of potassium bromide as catalyst and alkali metal compound, and 24.6 g. of 5-acetoxy-m-xylene (hereinafter referred to as merely "5-AMX") having a purity of 99.0% by weight.

With the reaction temperature maintained at 115° C., the reaction was caused to take place under the reaction pressure of 10 kg/cm$^2$ gauge until absorption of oxygen was no longer observed, during which period air was blown to the extent that the oxygen content in the exhaust gas stayed at 5% by volume.

Following completion of the reaction and after the autoclave was cooled to 40° C., the reaction mixture was taken out of the autoclave and cooled to room temperature (15° C.). Then, the solid which mainly comprises 5-acetoxyisophthalic acid (hereinafter referred to as "5-AIPA") was recovered by filtration, washed with a small amount of acetic acid and dried to obtain 30.0 g. of white 5-AIPA having a purity of 99.8% by weight. The yield of 5-AIPA was 95.7 mol % with respect to the raw material 5-AMX combined with the amount of 5-AIPA contained in mother liquor.

The test result is shown in Tables 1 and 2 along with the test results for other EXAMPLES and COMPARATIVE EXAMPLES.

EXAMPLE 2

5-AIPA was produced in the similar procedures as EXAMPLE 1, except that the amount of cobalt acetate tetrahydrate was 0.70 g., 0.92 g. of cobalt bromide hexahydrate was added, and 0.55 g. of potassium acetate was added instead of potassium bromide.

As the result, white 5-AIPA having a purity of 99.8% by weight was obtained at 95.1 mol % yield.

Comparative Example 1

5-AIPA was produced in the similar procedures as EXAMPLE 2, except that potassium acetate was not added. The 5-AIPA thus obtained was in yellowish white and had a purity of 93.4% by weight.

EXAMPLE 3

A reaction was carried out in the similar procedures as EXAMPLE 1, except that the selected pressure was 5 kg/cm$^2$ gauge. As the result, white 5-AIPA having a purity of 99.8% by weight was obtained at a yield of 91.0 mol %.

Comparative Example 2

A reaction was carried out at the pressure of 5 kg/cm$^2$ gauge after adding 5-AMX, acetic acid, acetic arthydride and cobalt acetate tetrahydrate in the respective quantities shown in Table 1. The yield thereby achieved was 37.2 mol %, and the 5-AIPA thus obtained was in yellow color and had a purity of 93.0% by weight.

EXAMPLE 4

A reaction was carried out in the similar procedures as EXAMPLE 1, except that potassium bromide was replaced by sodium bromide (0.58 g.) of an equivalent mol. As the result, white 5-AIPA was obtained at a yield of 95.0 mol %.

EXAMPLE 5

A reaction was carried out in the similar procedures as EXAMPLE 1, except that the amounts of cobalt acetate tetrahydrate and potassium bromide added were twice as much as in EXAMPLE 1. As the result, white 5-AIPA was obtained at a yield of 94.2 mol %.

Comparative Example 3

A reaction was carried out in the similar procedures as EXAMPLE 5, except that 0.29 g. of potassium acetate was added and also that the potassium-to-cobalt ratio (gram atom/gram atom) selected was 1.3. As the result, white 5-AIPA was obtained at a yield of 87.1 mol %.

Comparative Example 4

A reaction was carried out in the similar procedures as EXAMPLE 5, except that the amounts of cobalt acetate tetrahydrate and potassium bromide added were twice as much as in EXAMPLE 5, and the selected pressure was 30 kg/cm² gauge. Yellow 5-AIPA was obtained at a yield of 84.6 mol %.

Comparative Example 5

A reaction was carried out in the similar procedures as COMPARATIVE EXAMPLE 3, except that 1.60 g. of sodium bromide (sodium/cobalt ratio=1.4) was added in place of 1.34 g. of potassium bromide and that the selected reaction pressure was 30 kg/cm² gauge. Although yield was improved to 90.5 mol %, the obtained 5-AIPA was in yellowish white color.

EXAMPLE 6

A reaction was carried out in the similar procedures as EXAMPLE 3, using the same catalyst as was used in EXAMPLE 3, except that the amount of 5-AMX was 16.2 g. As the result, white 5-AIPA was obtained at a yield of 95.7 tool %.

EXAMPLE 7

A reaction was carried out in the similar procedures as EXAMPLE 1, using the same amount of the same catalyst as was used in EXAMPLE 1, except that the amounts of 5-AMX, acetic acid and acetic arthydride were as shown in Table 2. As the result, white 5-AIPA was obtained at a yield of 91.4 mol %.

Advantage of the Invention

Since, according to the present invention, high-quality 5-HIPA can be obtained at a high yield by means of air-oxidizing 5-acyloxy-m-xylene in the liquid phase under a pressure lower than that which is selected conventionally, using catalyst consisting of a cobalt compound and a bromine compound, wherein a specific amount of alkali metal compound is caused to co-exist, the said method has an immense value as an industrial scale process for producing 5-HIPA.

TABLE 1

|  |  |  | Example 1 | Example 2 | Example 3 | Example 4 | Example 5 | Example 6 |
|---|---|---|---|---|---|---|---|---|
| Quantity (g.) | 5-AMX |  | 24.6 | 24.6 | 24.6 | 24.6 | 24.6 | 16.2 |
|  | Solvent | Acetic acid | 170 | 170 | 170 | 170 | 170 | 170 |
|  |  | Acetic anhydride | 70 | 70 | 70 | 70 | 70 | 70 |
|  | Catalyst | Cobalt acetate tetrahydrate |  |  |  |  |  |  |
|  |  | Cobalt bromide hexahydrate |  |  | 0.92 |  |  |  |
|  |  | Sodium bromide |  |  |  |  | 0.58 |  |
|  |  | Potassium bromide | 0.67 |  | 0.67 |  | 1.34 | 0.67 |
|  |  | Ammonium bromide |  |  |  |  |  |  |
|  |  | Potassium acetate |  | 0.55 |  |  |  |  |
| Reaction condition |  | Oxidation agent | Air | Air | Air | Air | Air | Air |
|  |  | Temperature (°C.) | 115 | 115 | 115 | 115 | 115 | 115 |
|  |  | Pressure (kg/cm² gage) | 10 | 10 | 5 | 10 10 | 5 |  |
|  |  | Alkali metal/Heavy metal (g. atom/g. atom) | 1.0 | 1.0 | 1.0 | 1.0 | 1.0 | 1.0 |
| Results |  | 5-AIPA yield by mol % | 95.7 | 95.1 | 91.0 | 95.0 | 94.2 | 95.7 |
|  |  | Purity % by weight | 99.8 | 99.8 | 99.8 | 99.2 | 99.7 | 99.0 |
|  |  | Color | White | White | White | White | White | White |

TABLE 2

|  |  |  | Example 7 | Compara. Example 1 | Compara. Example 2 | Compara. Example 3 | Compara. Example 4 | Compara. Example 5 |
|---|---|---|---|---|---|---|---|---|
| Quantity (g.) | 5-AMX |  | 49.3 | 24.6 | 40 | 24.6 | 24.6 | 24.6 |
|  | Solvent | Acetic acid | 100 | 170 | 60 | 170 | 170 | 170 |
|  |  | Acetic anhydride | 140 | 70 | 90 | 70 | 70 | 70 |
|  | Catalyst | Cobalt acetate tetrahydrate | 1.40 | 0.70 | 0.91 | 2.80 | 5.60 | 2.80 |
|  |  | Cobalt bromide hexahydrate |  | 0.92 |  |  |  |  |
|  |  | Sodium bromide |  |  |  |  |  | 1.60 |
|  |  | Potassium bromide | 0.67 |  |  | 1.34 | 2.68 |  |
|  |  | Ammonium bromide |  |  | 0.42 |  |  |  |
|  |  | Potassium acetate |  |  |  | 0.29 |  |  |
| Reaction condition |  | Oxidation agent | Air | Air | Air | Air | Air | Air |
|  |  | Temperature (°C.) | 115 | 115 | 115 | 115 | 115 | 115 |
|  |  | Pressure (kg/cm² gage) | 10 | 10 | 5 | 10 | 30 | 30 |
|  |  | Alkali metal/Heavy metal (g. atom/g. atom) | 1.0 | 0 | 0 | 1.3 | 1.0 | 1.4 |
| Results |  | 5-AIPA yield by mol % | 91.4 | 88.1 | 37.2 | 87.1 | 84.6 | 90.5 |
|  |  | Purity % by weight | 98.7 | 93.4 | 93.0 | 98.7 | 92.3 | 94.1 |
|  |  | Color | White | Yellowish | Yellow | White | Yellow | Yellowish |

TABLE 2-continued

| | Example 7 | Compara. Example 1 | Compara. Example 2 | Compara. Example 3 | Compara. Example 4 | Compara. Example 5 |
|---|---|---|---|---|---|---|
| | | white | | | | white |

We claim:

1. A process for manufacturing 5-hydroxyisophthalic acid which comprises oxidizing 5-acyloxy-m-xylene or its oxidation intermediate with molecular oxygen in a solvent consisting of lower aliphatic carboxylic acid and acetic anhydride in the presence of catalyst consisting of heavy metal compound comprising cobalt as the main component, and a bromine compound, and hydrolyzing the product thereby obtained, which process is characterized in that the oxidation is carried out under a pressure of 2–15 kg/cm² gauge in the presence of an alkali metal compound corresponding to 0.1–1.1 gram atom in terms of the alkali metal atom based upon 1 gram atom of the heavy metal used for the catalyst.

2. The process for manufacturing 5-hydroxyisophthalic acid according to claim 1, wherein the 5-acyloxy-m-xylene is 5-acetoxy-m-xylene.

3. The process for manufacturing 5-hydroxyisophthalic acid according to claim 1, wherein the lower aliphatic carboxylic acid is acetic acid.

4. The process for manufacturing 5-hydroxyisophthalic acid according to claim 1, wherein the heavy metal compound is selected from the group consisting of cobalt acetate and cobalt bromide.

5. The process for manufacturing 5-hydroxyisophthalic acid according to claim 1, wherein the bromine compound is selected from the group consisting of sodium bromide, potassium bromide and ammonium bromide.

6. The process for manufacturing 5-hydroxyisophthalic acid according to claim 1, wherein the alkali metal compound is selected from the group consisting of sodium bromide, potassium bromide, sodium acetate and potassium acetate.

* * * * *